US011521316B1

(12) United States Patent
Farag et al.

(10) Patent No.: US 11,521,316 B1
(45) Date of Patent: Dec. 6, 2022

(54) AUTOMATIC EXTRACTION OF INTERDENTAL GINGIVA REGIONS

(71) Applicant: Kentucky Imaging Technologies, Louisville, KY (US)

(72) Inventors: Aly Farag, Louisville, KY (US); Mohamad Ghanoum, Louisville, KY (US); Asem Ali, Louisville, KY (US); Salwa Elshazly, Louisville, KY (US)

(73) Assignee: Kentucky Imaging Technologies, Louisville, KY (US)

( * ) Notice: Subject to any disclaimer, the term of this patent is extended or adjusted under 35 U.S.C. 154(b) by 187 days.

(21) Appl. No.: 16/840,074

(22) Filed: Apr. 3, 2020

Related U.S. Application Data

(60) Provisional application No. 62/828,629, filed on Apr. 3, 2019.

(51) Int. Cl.
*G06T 7/00* (2017.01)
*G06T 7/70* (2017.01)
*A61C 7/00* (2006.01)
*G06T 7/60* (2017.01)

(52) U.S. Cl.
CPC ............ *G06T 7/0012* (2013.01); *A61C 7/002* (2013.01); *G06T 7/60* (2013.01); *G06T 7/70* (2017.01); *A61C 2007/004* (2013.01); *G06T 2207/30036* (2013.01)

(58) Field of Classification Search
CPC ........... G06T 7/0012; G06T 7/60; G06T 7/70; G06T 2207/30036; A61C 7/002; A61C 2007/004
See application file for complete search history.

(56) References Cited

U.S. PATENT DOCUMENTS

| 6,909,913 | B2 | 6/2005 | Vining |
| 6,928,314 | B1 | 8/2005 | Johnson et al. |
| 7,194,117 | B2 | 3/2007 | Kaufman et al. |
| 7,194,393 | B2 | 3/2007 | Wei et al. |
| 7,304,644 | B2 | 12/2007 | Geiger |

(Continued)

OTHER PUBLICATIONS

Ghanoum et al., "Automatic Extraction of Interdental Gingiva Regions for Accurate Statistical Shape from Shading-based Reconstruction of Human Jaw", 2018 IEEE 15th International Symposium on Biomedical Imaging (ISBI 2018), pp. 998-1001 (Year: 2018).*

(Continued)

*Primary Examiner* — Nay A Maung
*Assistant Examiner* — Jose M Torres
(74) *Attorney, Agent, or Firm* — Law Office of J.L. Simunic; Joan Simunic

(57) ABSTRACT

The three-dimensional (3D) reconstruction of visible part of the human jaw is becoming required for many diagnostic and treatment procedures. The present invention improves upon Statistical Shape from Shading (SSFS) framework by using a novel approach to automatically extract prior information. This two-step framework consists of interdental gingiva regions extraction for each individual tooth and detection of the centerline across the jaw span. These two steps help extract the anatomical landmark points and detect the status of the jaw. Experimental results highlight the accuracy of the extracted prior information and how this information boosts recovering 3D models of the human jaw.

3 Claims, 7 Drawing Sheets

(56) References Cited

U.S. PATENT DOCUMENTS

| | | |
|---|---|---|
| 7,839,402 B2 | 11/2010 | Dekel et al. |
| 7,853,310 B2 | 12/2010 | Vining et al. |
| 7,961,187 B2 | 6/2011 | Borland et al. |
| 8,014,561 B2 | 9/2011 | Farag et al. |
| 8,041,141 B2 | 10/2011 | Farag et al. |
| 3,055,026 A1 | 11/2011 | Pedersen |
| 8,073,226 B2 | 12/2011 | Farag et al. |
| 8,150,111 B2 | 4/2012 | Borland et al. |
| 8,259,108 B2 | 9/2012 | Suhling et al. |
| 8,625,902 B2 | 1/2014 | Baheti et al. |
| 9,286,505 B2 | 3/2016 | Ajemba et al. |
| 9,501,709 B2 | 11/2016 | Ikeda |
| 9,659,405 B2 | 5/2017 | Wahrenberg |
| 10,242,488 B1 | 3/2019 | Farag et al. |
| 10,734,028 B2 | 8/2020 | Fay |
| 2002/0044689 A1 | 4/2002 | Roustaei et al. |
| 2005/0152588 A1 | 7/2005 | Yoshida et al. |
| 2005/0245803 A1 | 11/2005 | Glenn, Jr. et al. |
| 2007/0003131 A1 | 1/2007 | Kaufman |
| 2007/0052724 A1 | 3/2007 | Graham et al. |
| 2008/0055308 A1 | 3/2008 | Dekel et al. |
| 2008/0118117 A1 | 5/2008 | Gauldie et al. |
| 2008/0297509 A1 | 12/2008 | Matsumoto |
| 2009/0016589 A1 | 1/2009 | Wolf et al. |
| 2014/0146044 A1 | 5/2014 | Cvetko |
| 2016/0125651 A1* | 5/2016 | Lior .................... A61C 9/0053 382/154 |
| 2019/0333224 A1* | 10/2019 | Liu ...................... G06K 9/6256 |
| 2020/0320685 A1* | 10/2020 | Anssari Moin ........ G06V 10/82 |

OTHER PUBLICATIONS

Elhabian et al., "Appearance-based approach for complete human jaw shape reconstruction", IET Computer Vision, 2014, vol. 14, Iss. 5, pp. 404-418 (Year: 2014).*

Mohamed, Mostafa & Farag, Amal & Ali, Asem & Elshazly, Salwa & Farag, Aly & Ghanoum, Mohamad. (2018). Fly-In Visualization for Virtual Colonoscopy. 2062-2066. 10.1109/ICIP.2018.8451412.

M. Mohamad, A. Farag, A. M. Ali, S. Elshazly, A. A. Farag and M. Ghanoum, "Enhancing virtual colonoscopy with a new visualization measure," 2018 IEEE 15th International Symposium on Biomedical Imaging (ISBI 2018), Washington, DC, 2018, pp. 294-297, doi: 10.1109/ISBI.2018.8363577.

Buchaillard, Stephanie I, S H Ong, Yohan Payan, and Kelvin Foong, "3d statistical models for tooth surface reconstruction.," Computers in biology and medicine, 2007, vol. 37, No. 10, pp. 1461-1471.

Elhabian, Shireen Y. and Aly A. Farag, "Appearance based approach for complete human jaw shape reconstruction.," IET Computer Vision, 2014, vol. 8, No. 5, pp. 404-418.

Sporring, J. and K. H. Jensen, "Bayes reconstruction of missing teeth," Journal of Mathematical Imaging and Vision, 2008, vol. 31, No. 2-3, pp. 245-254.

Ghanoum, Mohamad, Asem M. Ali, Salwa Elshazly, Islam Alkabbany, Aly A. Farag, "Automatic Extraction of Interdental Gingiva Regions for Accurate Statistical Shape from Shading-based Reconstruction of Human Jaw", IEEE Conference Proceedings, 2018, pp. 998-1001.

* cited by examiner

Algorithm 1 Landmark points extraction

1: procedure FIND_LANDMARKS(Contour $C(p) = [x(p) \ y(p)]$:)
2:    for all $p$ in $C$ do
3:       $\kappa(p) = \frac{x_p y_{pp} - y_p x_{pp}}{(x_p^2 + y_p^2)^{3/2}}$   ▷ find Euclidean Curveture
4:    end for
5:    $IG = \{g \mid \kappa(g) \ is \ local \ minima\}$   ▷ find IG regions
6:    for all $g$ in $IG$ do
7:       $g\_pair = \arg\min_{q \in IG}(\|C(q) - C(g)\|_2)$
   s.t.   $C(q).C(g) \approx -1$
8:       if $g\_pair == \phi$ then
9:          $IG = IG - g$
10:      end if
11:   end for
12:   $B = \{median[DFS^*(a,b)] \ \forall a, b \ successive \ element \in IG\}$   ▷ Depth First Search path
13:   $landmarks = IG \cup B$
14:   return landmarks
15: end procedure

FIG. 3

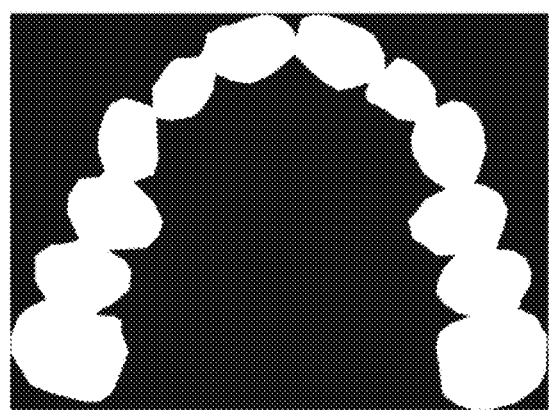
(a)
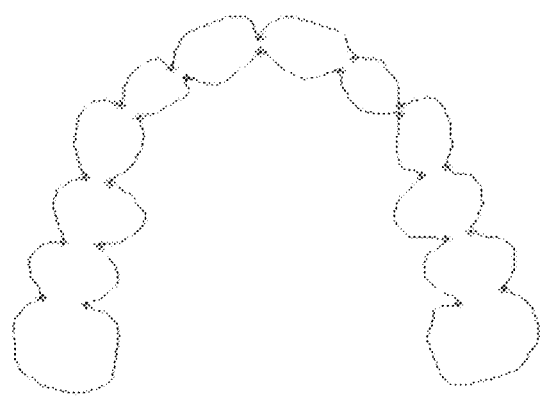
(b)
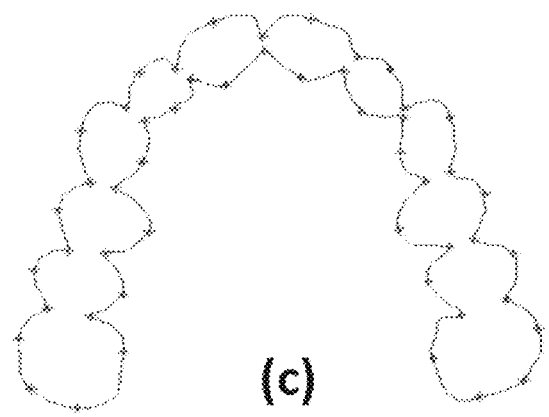
(c)
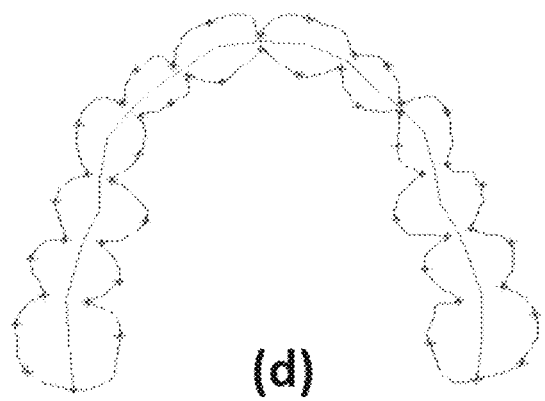
(d)
FIG. 4

AUTOMATIC EXTRACTION OF INTERDENTAL GINGIVA REGIONS

CROSS-REFERENCE TO RELATED APPLICATIONS

The present application claims priority to U.S. Patent Application 62/828,629 filed 2019 Apr. 3, which is incorporated by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM LISTING APPENDIX SUBMITTED ON COMPACT DISC AND AN INCORPORATION-BY-REFERENCE OF THE MATERIAL ON THE COMPACT DISC

Not applicable.

STATEMENT REGARDING PRIOR DISCLOSURES BY AN INVENTOR OR JOINT INVENTOR

The subject matter of the instant invention was described in an article authored by the present inventors entitled Automatic Extraction of Interdental Gingiva Regions for Accurate Statistical Shape from Shading-Based Reconstruction of Human Jaw and published in the 2018 IEEE 15$^{th}$ International Symposium on Biomedical Imaging (ISBI 2018) on 4 Apr. 2018. The publication was filed as provisional application U.S. 62/828,629. The publication is included on the Information Disclosure Statement filed 2 Jun. 2022 and a copy of the publication is provided therewith. All authors on the publication are inventors of the present development.

BACKGROUND OF THE INVENTION

(1) Field of the Invention

The present invention is a method to detect the centerline across the jaw span. The method comprises using an algorithm, disclosed herein, that automatically estimates the anatomical landmark points, the number of teeth per jaw, and the status of the jaw from an optical image of an occlusal surface by extracting the anatomical landmark points, thereby eliminating the need for manual annotations of this prior information.

(2) Description of Related Art Including Information Disclosed Under 37 CFR 1.97 And 37 CFR 1.98

To make it easy and feasible for doctors, dentists, and researchers to obtain a 3D model of a person's jaw without ionizing radiation, several works have been conducted to reconstruct the tooth occlusal surface based on a training database of 3D teeth. Blanz et al. (2004) proposed a statistical tooth-based model. The 3D shape model of a tooth is estimated by warping a set of training shapes. The warping process depends on a manually annotated set of landmarks. In a similar way, in order to have a point-to-point correspondence between different specimens, Buchaillard et al. (2007) manually aligned training teeth with a generic tooth. Then, the tooth shape is described by a point distribution model. Also, Sporring and Jensen (2008) manually selected a set of landmarks to reconstruct a tooth's shape using a statistical model. Zheng et al. (2011) used the teeth anatomical features to improve the snake model, which is used to extract features on the tooth surface. Elhabian and Farag (2014) proposed an appearance-based approach which allows for the reconstruction of plausible human jaw 3D models given a single optical image, which is augmented with manual landmark points for the jaw and clarify the jaw status with unknown illumination.

These previous works and a substantial amount of other work tried to exploit training database of 3D and 2D teeth in dental applications. However, these trails depend on manual annotations. The typical jaw has 32 individual teeth (28 if the wisdom teeth are removed), distributed into two rows (upper and lower) with basic symmetry. The teeth are divided into four primary categories: incisors, canines, premolars and molars, as illustrated in FIG. 1. Augmenting dental applications with manual landmark points for the jaw and clarifying the jaw status is a time-consuming process and is prone to human errors.

Many patents and patent applications have been submitted to propose automatic feature extraction methods and systems. In U.S. Pat. No. 9,286,505, systems and methods of feature extraction from tissue images, such as images of nuclei and/or cytoplasm, are introduced. A corrected image is generated by multiplying the tissue image by the inverse illumination field. This corrected image has fewer non-uniform intensity variations than the tissue image input. In U.S. Pat. No. 8,055,026, a method for extracting desired features from a cellular image is introduced. First an initial cell within the image is selected; then a region growing-like method is used to select cells appearing to be associated with said feature until selection termination criteria are satisfied. In U.S. Published Application 2002-0044689, an apparatus and method, in which a global feature extraction and local feature extraction is integrated to locate, identify and decode optical codes found within a captured image, are introduced. In U.S. Pat. No. 7,194,393, a numerical model for image feature extraction is introduced. In this method geometric patterns are generated from an image having a plurality of ridges and mesh points. The method includes dividing the image into a plurality of local regions with a surface appearance of fluid flow; establishing a mathematical model according to conditions of the plurality of local regions with a surface appearance of fluid flow; solving the mathematical model; and mapping respective values of the solutions of the mathematical model to respective local regions of the image. In U.S. Pat. No. 8,625,902, a method to extract keypoints from an image is taught. A first set of keypoints is extracted from blurred images of a first octave of a received image. Then a second set of keypoints is extracted from a second set of blurred images of a second octave of the received image. This is repeated as long as the confidence value does not exceed a threshold. Unlike these general-purpose feature extraction methods, which may fail to extract gingiva regions, this invention is designed to jaw geometry to extract the features of interest such as gingiva regions from the jaw image.

Lack of such a tool that automatically extracts teeth contour, anatomical landmarks of the human jaw, and jaw centerline, highlights the importance of this invention.

BRIEF SUMMARY OF THE INVENTION

The present development is a method that uses an algorithm, which is summarized in FIG. 3, to extract human jaw anatomical landmarks. Given a single optical image, the anatomical prior information is automatically extracted. Appearance bases are analytically constructed using the frequency-based representation of the irradiance equation while incorporating prior information about natural illumination and teeth reflectance. The inherent relation between the photometric information and the underlying 3D shape is formulated as a statistical model wherein the coupled effect of illumination and reflectance is modelled using the Helmholtz hemispherical harmonics-based irradiance harmonics whereas the principal component regression is deployed to carry out the estimation of 3D shapes.

BRIEF DESCRIPTION OF THE SEVERAL VIEWS OF THE DRAWING

For a more complete understanding of the invention, reference is made to the following description and accompanying drawings, in which:

FIG. 3 is a summary of the Landmarks Extraction Algorithm;

FIG. 4 shows the processing steps of the proposed method wherein (a) shows the input binary image, (b) shows the results of extracting the contour and estimating the highest curvature points, (c) shows the results of estimating the border points, and (d) shows the results of extracting the center line;

DETAILED DESCRIPTION OF THE INVENTION

The three-dimensional (3D) reconstruction of the visible part of the human jaw is becoming required for many of diagnostics and treatment procedures. Dentistry requires accurate 3-D representations of the teeth and jaw for diagnostic and treatment purposes. In order to evaluate tooth movement progress, the orthodontist monitors this movement by mean visual inspection, intra oral measurement, fabrication of casts, photographs, and radiographs. This process is both costly and time-consuming. There has been a substantial amount of work to make it easy and feasible for doctors, dentists, and researchers to obtain 3D model of the person's jaw based on a training database of 3D teeth and without ionizing radiation. The main drawback, in these several works, is the need for a manually annotated set of landmarks, which is time consuming and prone to human errors. This invention boosts these methods by proposing a novel method to automatically extract the prior information.

Figure 6:
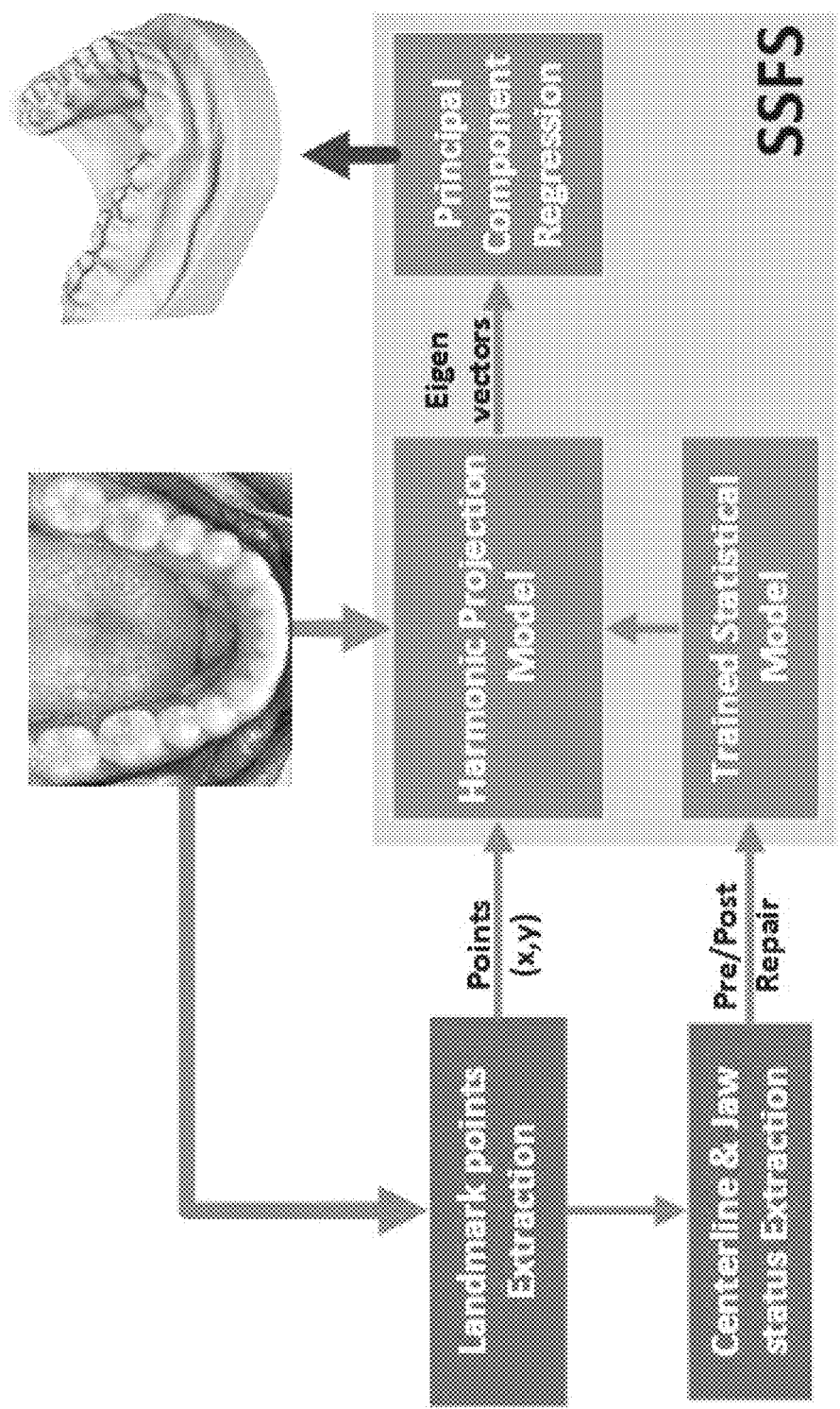
FIG. 6 is an illustration of an example embodiment showing an automatic statistical shape from shading approach for 3D jaw reconstruction; and, FIG. 7 is an illustration of the estimated and the ground truth of the centerline and the landmark points.
Figure 7:
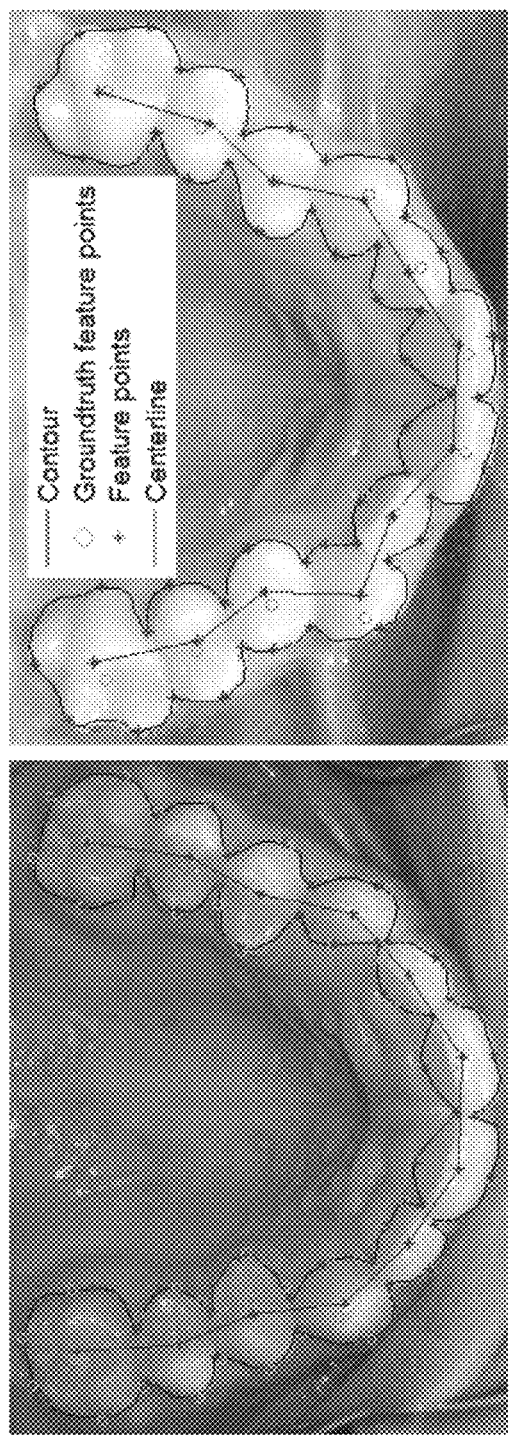

As shown in FIG. 6, the present development is an appearance-based approach, which allows for the reconstruction of plausible human jaw 3D models given a single optical image with unknown illumination. The number of teeth per jaw (e.g., 14 or 12), the jaw status and the anatomical landmark points around each tooth are automatically estimated using this invention. First, the anatomical landmark points (IG) are automatically extracted. Then the number of teeth is estimated using the extracted IG points. Finally, the jaw status is automatically detected as either 'pre-repair' (as shown in FIG. 7(b)) or 'post-repair' (as shown in FIG. 7(a)), which refers to 'before' or 'after' applying an orthodontic teeth alignment process, respectively. The jaw is considered to be pre-repair if the Euclidean curvature of the centerline has more than one maximum point.

Figure 1:
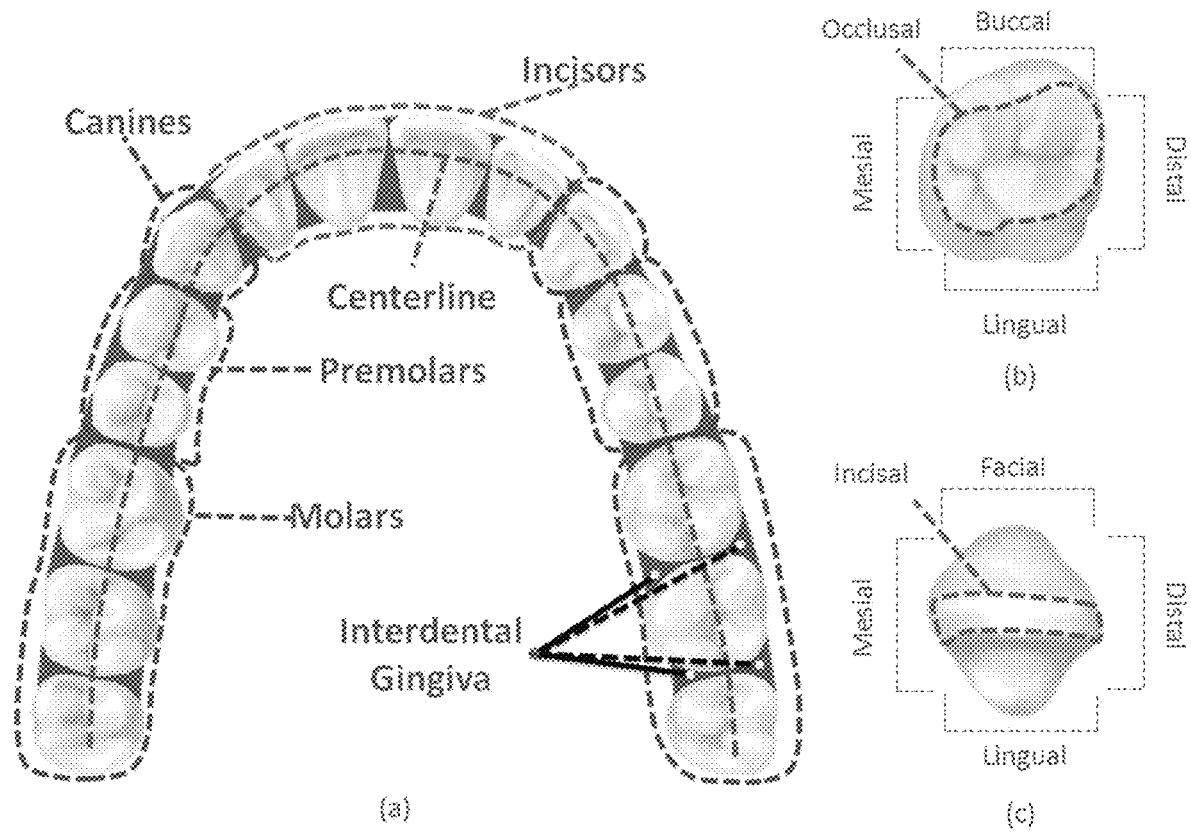
FIG. 1 shows human teeth: (a) jaw anatomy, (b) molar tooth anatomy, and (c) incisor tooth anatomy.
Figure 2:
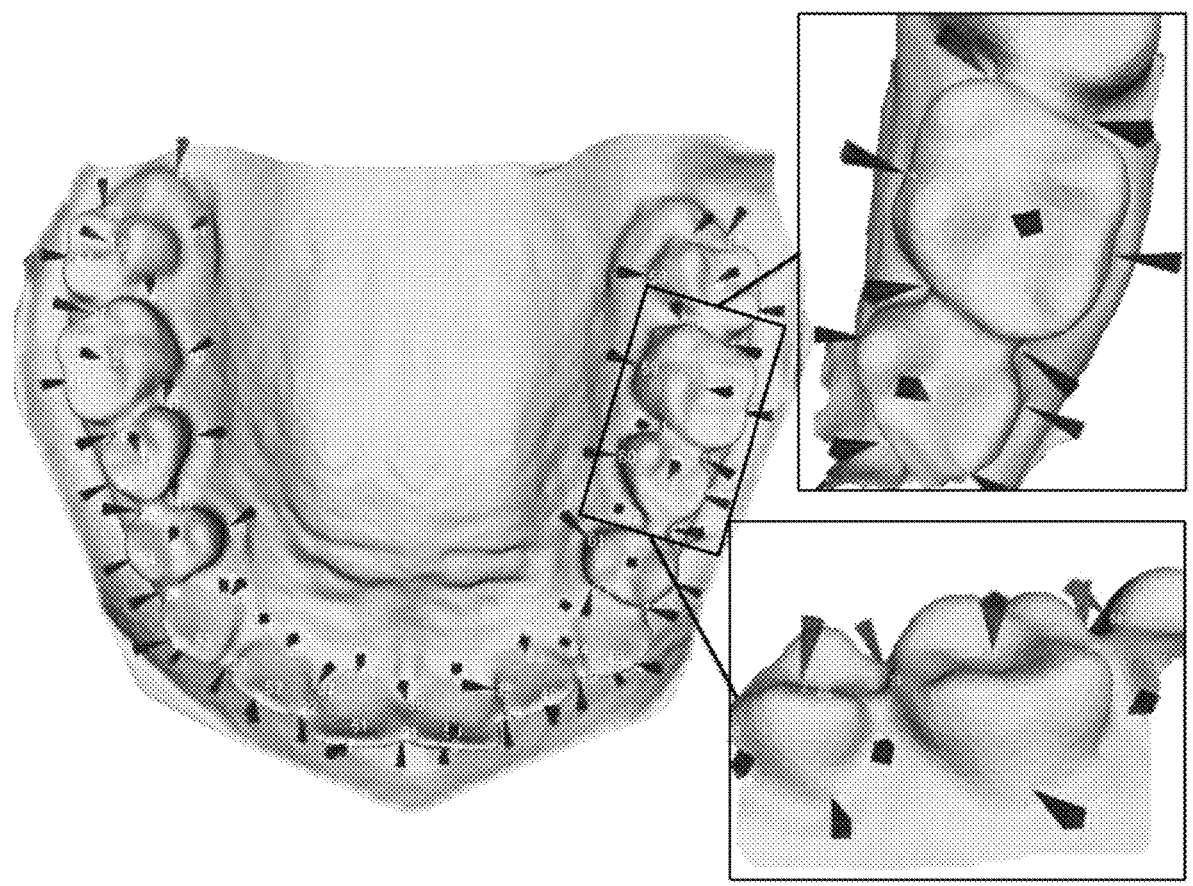
FIG. 2 is an illustration of the anatomical landmarks of human jaw.

More specifically, the present development uses an algorithm, which is summarized in FIG. 3, to extract human jaw anatomical landmarks. As is known in the art, the jaw's anatomical landmarks can be identified on the tooth surface or on the interface between the tooth and the gum. In this invention, 72 anatomical landmarks are defined for a jaw containing 14 teeth. These landmarks are shown on a 3D human jaw in FIG. 2. The centerline (see FIG. 1) is an anatomic curvature of the occlusal alignment of the teeth, beginning at the center of the lingual surface of the incisor, following the occlusal of the natural premolars and continuing to the molars. The centerline can help in detecting the status of the jaw.

Given a 2D RGB image of a human jaw, a segmented Black and White (BW) binary 2D image is generated and is used to estimate a Euclidean distance transform for a tooth's pixels (see FIG. 4(a)). This Euclidean distance transform gives each pixel a weight that is inversely proportional to its distance, such that the pixel on the edge of the tooth ha a higher weight than the ones in the middle. Using edge pixels, the contour of teeth, see FIG. 4(b), is extracted by removing all 4 connected pixels thus leaving only boundary pixels intact.

Figure 5:
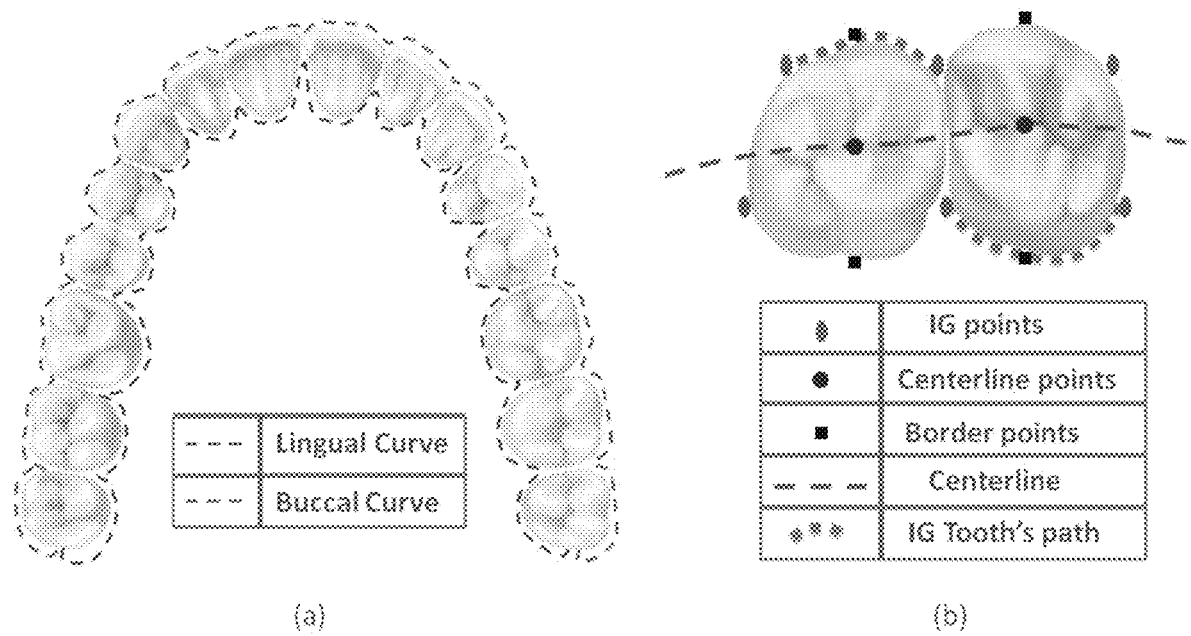
FIG. 5 is an illustration of the proposed human jaw anatomical landmarks wherein (a) shows the Curves definition, and (b) shows the Landmark points of the tooth.

The landmark points of the jaw are then extracted. For each point p=[x(p), y(p)] on a parametric contour C(p), the Euclidean curvature $$\kappa(p) = \frac{x_p y_{pp} - y_p x_{pp}}{\left(x_p^2 + y_p^2\right)^{2/3}},$$

where $x_P$ and $x_{pp}$ are the first and second derivative in the x-direction, is calculated. The Euclidean curvature at the interdental gingiva has a local minima value, so one point will be voted to represent each Interdental Gingiva (IG) area (see FIGS. 4(c) and 4(b)). The set of extracted Interdental Gingiva (IG) points is defined by G. Each IG point g at the Lingual curve (see FIG. 5(a)) has a pairwise IG point q at the Buccal curve that satisfies $$\underset{q \in G}{\operatorname{argmin}}(\|\tilde{C}(q) - \tilde{C}(g)\|_2)$$

such that C(q). C(g)≈−1. Assigning IG pairwise for each IG in the jaw generates accurate IG points and removes unpleased spurious points. After extracting four IG points around a tooth, still we have two remaining border points (see FIG. 5(b)). The IG tooth's path is estimated using the Depth First Search (DFS) algorithm, by moving from one IG point to another. The center point of this path is considered as the border point (see FIG. 4(c)).

After extracting two paths between the IG points on the Lingual and Buccal curves (see FIG. 4(c)) of the same tooth, the center point of a tooth is estimated by calculating the center mass of these two paths' points of that tooth. However, using only the center points of the teeth to localize the centerline is still inaccurate. So, the center points of the teeth are augmented with the center point of the straight line between the IG point on the Lingual curve and its pair on the Buccal curve (see FIG. 4(d)). Finally, using the Euclidean curvature of the centerline the jaw status is detected. If the centerline has multiple local maxima or minima points, this is indicative that the teeth need orthodontic treatment.

In an exemplary application of the method, the jaw's contour, anatomical landmarks, and centerline are determined using the present invention with automatically extracted information from a single optical image of the jaw and the result was compared to the prior art Statistical Shape from Shading (SSFS) method using ground-truth landmark points that are manually annotated. The dataset comprises 177 jaw optical images (94 lower and 83 upper) representing 83 subjects. For these images the ground-truth landmark points were manually annotated, while the ground-truth for the 3D shape was obtained by CT scan. The dataset was divided according to the number of teeth per jaw to 61 images of jaws that have 12 teeth, and 116 images of jaws that have 14 teeth. The dataset was also divided according to the jaw status to 'pre-repair' and 'post-repair' jaw images. The ground truth of the landmark points was annotated manually and divided into three groups: (1) Centroid teeth points, which represent the center of top surface teeth, (2) Border points which represent the edge between the gum and side surfaces of the teeth, and (3) IG points which represent the triangular wedge between two adjacent teeth. For accurate evaluation, the extracted landmark points around the teeth and the centerline points were categorized into these three groups. The localization accuracy was assessed using the cumulative distribution of the normalized error, wherein the normalized error is the distance between the detected landmark point and the manually annotated point (ground truth) divided by the tooth width, which can be calculated from its border points. Using this dataset, the cumulative error distributions were computed for the three groups. It was observed that the errors in estimating the centerline points are less than the errors in estimating the border and IG points because the ground truth landmarks are manually annotated on RGB images, in which the border points are unclear, unlike at the tooth's center. To further assess the accuracy of the present invention, the RMS errors in mm between the 3D points from the 177 CT scans and the corresponding reconstructed surface points were computed. Table 1 reports the average and the standard deviation of these RMS errors for the inventive method and for the original SSFS method. It was observed that the error values of the reconstructions recovered by the inventive method are minimal when compared with the ones recovered by the original SSFS model.

TABLE 1

Average and std of whole jaw reconstruction accuracy (RMS) in mm

| Jaw Type | Original SSFS | Present Method |
|---|---|---|
| Upper, 12 teeth | 0.9686 ± 0.6031 | 0.9415 ± 0.1667 |
| Upper, 14 teeth | 0.7873 ± 0.3571 | 0.6227 ± 0.2157 |
| Lower, 12 teeth | 0.7390 ± 0.1966 | 0.6085 ± 0.0628 |
| Lower, 14 teeth | 0.8195 ± 0.3457 | 0.6612 ± 0.1158 |

The present development is a method for estimating the status of the jaw from an optical image of an occlusal surface by extracting anatomical landmarks to detect the centerline across the jaw span. The present method improves upon Statistical Shape from Shading (SSFS) framework by using a novel approach to automatically extract the relevant information thereby eliminating the need for manual annotation which saves time and results in improved accuracy.

What is claimed:

1. A method for estimating the jaw status for an orthodontic treatment, the method comprising:
   a. estimating a Euclidean distance transform for a tooth's pixels to give each pixel a weight;
   b. extracting the contour of teeth and leaving only boundary pixels intact;
   c. detecting interdental gingiva (IG) points from the contour;
   d. assigning IG pairwise for each IG in the jaw to generate accurate IG points and remove unpleased spurious points;
   e. extracting two paths between the IG points on the Lingual and Buccal curves of the same tooth;
   f. estimating the center point of a tooth by calculating the center mass of these two paths' points of that tooth;
   g. defining a centerline by connecting the center points on adjacent teeth; and
   h. estimating the jaw status using the Euclidean curvature of the centerline.

2. The method of claim 1 wherein a segmented Black and White (BW) binary 2D image is used to estimate the Euclidean distance transform for the tooth's pixels.

3. The method of claim 1 wherein the tooth's pixel weight is inversely proportional to its distance.

* * * * *